United States Patent [19]

Carron et al.

[11] 4,356,130
[45] Oct. 26, 1982

[54] TREATING THE RESIDUE FROM THE PRODUCTION OF PHOSPHOROCHLORIDOTHIONATES

[75] Inventors: Mark S. Carron, Spring Valley; Ronald S. La Barbera, New City; Lester P. Van Brocklin, Thiells, all of N.Y.; Pawan K. Jain, Norwood, N.J.

[73] Assignee: Stauffer Chemical Company, Westport, Conn.

[21] Appl. No.: 193,247

[22] Filed: Oct. 2, 1980

[51] Int. Cl.$^3$ .................................................. C07F 9/20
[52] U.S. Cl. ..................................... 260/989; 260/986
[58] Field of Search ............................................ 260/989

[56] References Cited

FOREIGN PATENT DOCUMENTS 2912143 10/1980 Fed. Rep. of Germany ...... 260/990

OTHER PUBLICATIONS

Chem. Abstract of U.S. 2,794,703.

Primary Examiner—Anton H. Sutto

[57] ABSTRACT

The invention is a novel method of treating the distillation residue from the production of phosphorochloridothionates which comprises contacting the residue with a sufficient amount of a separating solution having a specific gravity of about 1.5, preferably phosphoric acid, to produce an organic layer which is easily separated from the remaining residue. The organic layer can be chlorinated to produce additional phosphorochloridothionate product.

12 Claims, No Drawings

TREATING THE RESIDUE FROM THE PRODUCTION OF PHOSPHOROCHLORIDOTHIONATES

BACKGROUND OF THE INVENTION

1. Field of the Invention

The invention in general pertains to the production of dialkyl or diaryl phosphorochloridothionates and, in particular, to a method for treating the residue from phosphorochloridothionate production and the recovery of additional product therefrom.

2. Prior Art

It has been suggested in the prior art to use the distillation residue from dialkyl phosphorochloridothionate production to produce additional thionate product (see British Pat. No. 1,245,052; U.S. Pat. Nos. 4,025,586 and 4,078,023).

British Pat. No. 1,245,052 discloses a method removing the sulfur from the residue and using the remaining residue as additional feed material for further product recovery. The sulfur is said to be in liquid form prior to separation from the residue mixture.

U.S. Pat. No. 4,078,023 discloses separating liquid sulfur from the residue after chlorination and distilling the residue prior to recycling the distillation portion of the residue for additional product recovery.

Recycling the residue as disclosed in the above cited art causes hydrolyzable impurities to accumulate, particularly the polymerized sulfur compounds which do not separate out with simple phase separation. U.S. Pat. No. 4,025,586 addresses the problem of the buildup of hydrolyzable impurities by washing the residue with water, after separation from the solid elemental sulfur, to remove the hydrolyzable impurities and thereafter drying the residue prior to recycling it for chlorination. The disclosure specifies the use of known means for separating the solid sulfur from the residue and discloses as an example centrifugation.

In some processes for making dialkyl phosphorochloridothionates, there is obtained a reaction mixture comprising amorphous, generally polymeric sulfur, which is generally, but not necessarily, in solution in an inert liquid reaction medium of the dialkyl phosphorochloridothionate product. The product is recovered by distillation leaving a distillation residue comprised of sulfur, which depending on the purity of the initial reactants is either in a liquid or a plastic solid state; other unstable organophosphorus byproducts; amounts of bis(thiophosphono)sulfide or polysulfide; and small amounts of the dialkyl or diaryl phosphorochloridothionate product.

One method of producing phosphorochloridothionates is from a corresponding phosphorodithioic acid intermediate produced by reacting $P_2S_5$ with an alcohol. It is generally desirous to use very pure reactants and maintain accurate reaction conditions to obtain high product yields and minimize the amount of side reaction products (impurities), formed in the process. The product is generally separated by fractional distillation leaving a distillation residue comprised of the liquid or solid sulfur and other unstable organophosphorus compounds. If the starting materials are pure and precise reaction conditions are maintained, the reaction products will generally contain reduced amounts of impurities and could possibly be immediately separated from the remaining distillation residue by phase separation. More generally however, the commercial process utilizes reactants which contain varying amounts of impurities, and reaction conditions may also vary somewhat. The distillation residue obtained under such conditions will generally comprise a mixture of solid plastic amorphous sulfur in a liquid comprised of organophosphorous bearing compounds and other dissolved polymeric sulfur compounds. Sulfur, especially solid amorphous sulfur is very difficult to separate from the other components of the distillation residue by conventional methods.

It is an object of the invention to provide means for separating the solid amorphous sulfur from the distillation residue where by the unreacted bis(thiophosphono)sulfide and the remaining dialkyl phosphorochloridothionate product can be recovered and recycled.

SUMMARY OF THE INVENTION

The invention comprises a method of treating the distillation residue from the production of dialkyl or diaryl phosphorochloridothionates whereby it can be utilized for the recovery of additional product by subsequent chlorination. The disclosed invention comprises the steps of (a) mixing the hot residue with a sufficient amount of a separating solution having a requisite specific gravity to cause a three phase mixture to form comprising an organic phase, a separating solution phase and a sulfur phase; (b) recovering an organic phase which is of a lower specific gravity than the separation solution. Additional phosphorochloridothionate production can be obtained by drying the organic layer and thereafter chlorinating the organic layer. The preferred separating solution to be utilized in the practice of the invention is phosphoric acid having a 30–90% concentration.

DETAILED DESCRIPTION OF THE INVENTION

A simple method for treating the unstable distillation residue from the production of phosphorochloridothionates has been discovered.

The method provides a convenient way for separating the sulfur from the residue which includes converting plastic amorphous sulfur into crystalline sulfur prior to the separation and also provides a means whereby the separation can be conveniently performed by simple phase separation.

The invention is based on the discovery that when the hot residue is mixed with a sufficient amount of a separating solution having a specific gravity greater than the organic constituents of the residue, a slurry will form, and that once agitation ceases at some time thereafter, an organic phase will separate from the solid crystalline sulfur phase, and the separating solution phase as a top layer.

The use of a separating solution having a specific gravity generally between about 1.2 and 1.8 causes the organic phase to float as a top layer which makes separation and removal easy and efficient. The specific gravity of the separating solution should generally be greater than that of the organic phase but less than the sulfur phase (about 1.8). Contact of the residue with the separating solution could also remove undesirable water soluble phosphates from the organic phase if the separating solution contains water or the organic phase can later be washed with water.

The separating solution, to be utilized in practicing the invention, therefore, should have a specific gravity between that of the organic phase and the sulfur phase formed, for the particular residue being treated. It should be essentially insoluble in both phases. The ratio of the separating solution to residue should be sufficient to cause a distinct three phase separation, and can be as low as 1:5 although, such a low ratio would not be recommended. A ratio of about 1:1 to 2:1 is preferred. It is also preferred to use a separating solution of sufficiently low temperature to quench the sulfur, and of sufficiently high volume to absorb the heat of crystallization of the sulfur.

Although phosphoric acid is the preferred separating solution for practicing the invention other solutions meeting the requisite specific gravity requirement such as sulfuric acid, salt solutions, or even certain solutions of organic compositions can be utilized.

In the practice of the invention, phosphoric acid having a 30-90% and preferably a 65-70% concentration and specific gravity of from about 1.2-1.8 and preferably 1.5 is available as a byproduct from the existing phosphorochloridothionate production process.

Phosphoric acid is obtained as a byproduct when the residue, remaining after the organic phase has been removed in accordance with the disclosed invention, is hydrolyzed.

The invention is applicable to the distillation residue from the production of dialkyl or diaryl phosphorochloridothionates and in particular for treating the residue from processes disclosed in U.S. Pat. Nos. 3,794,703; 3,897,523 and 4,185,053, all incorporated herein by reference.

In accordance with the disclosed invention, the distillate residue from the production of phosphorochloridothionates having the formula:

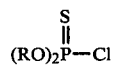

wherein R is an alkyl or aryl or substituted alkyl or aryl hydrocarbon radical is mixed with a sufficient amount of a separating solution preferably phosphoric acid, having a temperature within the range of 10°-100° C. The phosphoric acid can have a concentration within the range of 30-90% preferably, 65 to 70% concentration and is generally obtained as a byproduct of the phosphorochloridothionate production processes.

It should be evident to one having skill in the art that the temperature (within the 10°-100° C. range) of the separating solution used, will depend on the specific phosphorochloridothionate product residue treated in accordance with the disclosed invention. The residue of phosphorochloridothionates, having an increasing number of carbon atoms on their R groups can, of course, be treated at higher temperatures than possible with residues from dimethyl or diethyl phosphorochloridotionate production.

It should also be evident that the separating solution used in the practice of the invention should be one which will have minimum reactivity with the bis(thiophosphono)sulfide or polysulfide or with the phosphorochloridothionate product content of the residue.

The slurry formed as a result of mixing the hot residue with cold phosphoric acid is allowed to settle into a three phase mixture with an organic phase or layer at the top of phosphoric acid layer and a crystalline sulfur layer below the phosphoric acid layer. By simple phase separation, the organic layer can be removed leaving the phosphoric acid and sulfur. It is also within the scope of the invention to recover additional product by the chlorination of the recovered organic layer. It is preferable to wash the organic layer with water if the separating solution does not contain free water, otherwise water washing is not necessary for hydrolyzing the impurities. The wash water used should be at a sufficiently low temperature such that decomposition of the phosphorochloridothionate will be minimized during washing. After separation and water washing (where necessary) the organic layer is dried prior to chlorination.

In the product recovery process disclosed herein, the organic phase is recycled to a chlorinator and chlorinated. The recovered organic phase can be recycled to a second stage chlorination zone in a continuous process or semi-continuous process, or incorporated with the initial reactants in a batch process all as disclosed in U.S. Pat. Nos. 3,794,703; 3,897,523 or 4,185,053 previously incorporated herein by reference. The chlorinated organic phase contains some dialkyl phosphorochloridothionate left over from the previous distillation process and dialkyl phosphorochloridothionate formed in the chlorinator. The chlorinated organic phase is then distilled to produce dialkyl phosphorochloridothionates. The chlorination and distillation can be accomplished in existing equipment and the residue from this chlorination process hydrolyzed. The sulfur from the residue batch treated in the manner disclosed can be resuspended in the phosphoric acid. The phosphoric acid-sulfur slurry, and the wash is then reheated to melt the sulfur and hydrolyze the phosphate impurities contained therein. The liquid sulfur and phosphoric acid is then removed to a separator where the sulfur and phosphoric acid are recovered.

What is claimed is:

1. A method for treating the distillation residue from the production of dialkyl and diaryl phosphorochloridothionates comprising:
    (a) mixing the hot residue with a sufficient amount of a separating solution having a specific gravity to cause a three phase mixture to form comprised of an organic phase, a separating solution phase and a sulfur phase; and
    (b) recovering an organic phase which is of a lower specific gravity than the separating solution phase.

2. The method of claim 1 wherein the residue is from the production of dimethyl phosphorochloridothionate.

3. The method of claim 1 wherein the residue is from the production of diethyl phosphorochloridothionate.

4. The method of claim 2 or 3 wherein the separating solution has a specific gravity of from about 1.2-1.8.

5. The method of claim 2 or 3 wherein the separating solution has a specific gravity of from about 1.5.

6. The method of claim 1 or 2 or 3 wherein the separating solution is phosphoric acid.

7. The method of claim 6 wherein the phosphoric acid has a concentration of from 30-90%.

8. The method of claim 7 wherein the phosphoric acid has a concentration of from 65-70%.

9. The method of claim 1 wherein the separating solution is sulfuric acid.

10. The method of claim 1 wherein the separating solution has a temperature of from about 10°-100° C.

11. The method of claim 1 wherein the separating solution has a specific gravity less than the organic phase but greater than the sulfur phase.

12. The method of claim 1 wherein the ratio of separating solution to residue is from about 1:1 to 2:1.

* * * * *